(12) United States Patent
Zhang et al.

(10) Patent No.: US 11,311,852 B2
(45) Date of Patent: *Apr. 26, 2022

(54) DEVICE AND METHOD FOR PREPARING PARA-XYLENE AND CO-PRODUCING LIGHT OLEFINS FROM METHANOL AND/OR DIMETHYL ETHER AND TOLUENE

(71) Applicant: DALIAN INSTITUTE OF CHEMICAL PHYSICS, CHINESE ACADEMY OF SCIENCES, Liaoning (CN)

(72) Inventors: Tao Zhang, Liaoning (CN); Mao Ye, Liaoning (CN); Zhongmin Liu, Liaoning (CN); Jinling Zhang, Liaoning (CN); Hailong Tang, Liaoning (CN); Jinming Jia, Liaoning (CN); Changqing He, Liaoning (CN); Xiangao Wang, Liaoning (CN); Cheng Zhang, Liaoning (CN); Hua Li, Liaoning (CN); Yinfeng Zhao, Liaoning (CN); Chenggong Li, Liaoning (CN)

(73) Assignee: Dalian Institute of Chemical Physics, Chinese Academy of Sciences, Liaoning (CN)

( * ) Notice: Subject to any disclaimer, the term of this patent is extended or adjusted under 35 U.S.C. 154(b) by 98 days.

This patent is subject to a terminal disclaimer.

(21) Appl. No.: 16/608,819

(22) PCT Filed: Nov. 24, 2017

(86) PCT No.: PCT/CN2017/112809
§ 371 (c)(1),
(2) Date: Oct. 26, 2019

(87) PCT Pub. No.: WO2018/196360
PCT Pub. Date: Nov. 1, 2018

(65) Prior Publication Data
US 2020/0179891 A1 Jun. 11, 2020

(30) Foreign Application Priority Data
Apr. 27, 2017 (CN) .......................... 201710289046.3

(51) Int. Cl.
*B01J 8/18* (2006.01)
*B01J 8/00* (2006.01)
(Continued)

(52) U.S. Cl.
CPC ........... *B01J 8/1827* (2013.01); *B01J 8/0055* (2013.01); *B01J 8/26* (2013.01); *C07C 1/22* (2013.01);
(Continued)

(58) Field of Classification Search
CPC . B01J 8/1827; B01J 8/0055; B01J 8/26; B01J 2208/00761; B01J 2208/00938;
(Continued)

(56) References Cited

U.S. PATENT DOCUMENTS 2,453,740 A * 11/1948 Becker ................... B01J 8/1836
549/249
2,893,849 A 7/1959 Krebs
(Continued)

FOREIGN PATENT DOCUMENTS

CN 1326430 A 12/2001
CN 101239868 A 8/2008
(Continued)

*Primary Examiner* — Huy Tram Nguyen
(74) *Attorney, Agent, or Firm* — Seed IP Law Group LLP (57) ABSTRACT

Disclosed are a fast fluidized bed reactor, device and method for preparing para-xylene and co-producing light olefins from methanol and/or dimethyl ether and toluene, with the reactor, device and method being capable of solving or (Continued)

improving the problem of competition between an alkylation reaction and an MTO reaction during the process of producing the para-xylene and co-producing light olefins from toluene and methanol, thus achieving a synergistic effect between the MTO reaction and the alkylation reaction. By controlling the mass transfer and reaction, the competition between the alkylation reaction and the MTO reaction is coordinated and optimized to achieve a synergistic effect, thereby increasing the conversion rate of toluene, the yield of para-xylene and the selectivity of the light olefins. The fast fluidized bed reactor comprises a first reactor feed distributor and a plurality of second reactor feed distributors, the first reactor feed distributor and the plurality of second reactor feed distributors are sequentially arranged along the gas flow direction in a reaction zone of the fast fluidized bed reactor.

20 Claims, 1 Drawing Sheet

(51) Int. Cl.
*B01J 8/26* (2006.01)
*C07C 1/22* (2006.01)
*C07C 2/86* (2006.01)

(52) U.S. Cl.
CPC .............. *C07C 2/864* (2013.01); *C07C 2/865* (2013.01); *B01J 2208/00761* (2013.01); *B01J 2208/00938* (2013.01); *C07C 2529/40* (2013.01)

(58) Field of Classification Search
CPC .. B01J 8/18; B01J 8/1872; B01J 2208/00893; B01J 2208/023; B01J 8/24; C07C 1/22; C07C 2/864; C07C 2/865; C07C 2529/40; C07C 1/20; C07C 2/86; C07C 11/04; C07C 11/06; C07C 11/08; C07C 15/08; C07C 1/24; Y02P 20/584; Y02P 20/52; Y02P 30/20; Y02P 30/40
USPC .......................................................... 422/139
See application file for complete search history.

(56) References Cited

U.S. PATENT DOCUMENTS

| | | | |
|---|---|---|---|
| 2,953,517 A * | 9/1960 | Whiteley | C10B 55/10 208/127 |
| 4,070,393 A | 1/1978 | Angstadt et al. | |
| 4,337,120 A | 6/1982 | Spars et al. | |
| 4,456,504 A | 6/1984 | Spars et al. | |
| 4,691,031 A | 9/1987 | Suciu et al. | |
| 5,489,732 A | 2/1996 | Zhang et al. | |
| 5,939,597 A | 8/1999 | Dessau et al. | |
| 5,965,765 A | 10/1999 | Kurihara et al. | |
| 6,642,426 B1 | 11/2003 | Johnson et al. | |
| 9,095,831 B2 | 8/2015 | Han et al. | |
| 10,626,062 B2* | 4/2020 | Ye | B01J 29/85 |
| 10,640,433 B2* | 5/2020 | Zhang | B01J 8/00 |
| 10,702,841 B2* | 7/2020 | Ye | C07C 1/24 |
| 10,710,940 B2* | 7/2020 | Zhang | B01J 8/1872 |
| 11,084,765 B2* | 8/2021 | Ye | B01J 8/1863 |
| 2010/0016648 A1 | 1/2010 | Qi et al. | |
| 2011/0092756 A1 | 4/2011 | Lattner et al. | |
| 2011/0218373 A1 | 9/2011 | Qi et al. | |
| 2013/0165724 A1 | 6/2013 | Han et al. | |
| 2017/0001164 A1 | 1/2017 | Zhang et al. | |
| 2019/0256439 A1 | 8/2019 | Zhang et al. | |
| 2019/0263730 A1 | 8/2019 | Zhang et al. | |
| 2020/0055014 A1 | 2/2020 | Ye et al. | |

FOREIGN PATENT DOCUMENTS

| | | | |
|---|---|---|---|
| CN | 101239870 A | 8/2008 | |
| CN | 101260013 A | 9/2008 | |
| CN | 102372569 A | 3/2012 | |
| CN | 102463084 A | 5/2012 | |
| CN | 102463086 A | 5/2012 | |
| CN | 102464550 A | 5/2012 | |
| CN | 102464557 A | 5/2012 | |
| CN | 102895923 A | 1/2013 | |
| CN | 103028449 A | 4/2013 | |
| CN | 202962437 U | 6/2013 | |
| CN | 103588601 A | 2/2014 | |
| CN | 104107671 A | 10/2014 | |
| CN | 104549073 A | 4/2015 | |
| CN | 104549074 A | 4/2015 | |
| CN | 104672045 A | 6/2015 | |
| CN | 105985209 A | 10/2016 | |
| CN | 106588527 A | 4/2017 | |
| CN | 107961743 A | 4/2018 | |
| CN | 107961745 A | 4/2018 | |
| DE | 102006049546 A1 * | 4/2008 | ............ B01J 8/006 |
| JP | 55-144088 A | 11/1980 | |
| JP | 2012-206955 A | 10/2012 | |
| JP | 2014-531400 A | 11/2014 | |
| JP | 2017-504654 A | 2/2017 | |
| KR | 10-2014-0027512 A | 3/2014 | |
| TW | 2004-24136 A | 11/2004 | |
| WO | 02/25201 A1 | 3/2002 | |
| WO | WO2011049765 A2 | 4/2011 | |
| WO | 2013/016396 A3 | 1/2013 | |
| WO | 2015/094697 A1 | 6/2015 | |

\* cited by examiner

DEVICE AND METHOD FOR PREPARING PARA-XYLENE AND CO-PRODUCING LIGHT OLEFINS FROM METHANOL AND/OR DIMETHYL ETHER AND TOLUENE

TECHNICAL FIELD

The present invention relates to a device and a production method for producing para-xylene (PX) and co-producing light olefins, and is particularly suitable for a fluidized bed device and a production method for preparing the para-xylene and co-producing the light olefins by the alkylation of methanol and/or dimethyl ether and toluene, which belongs to the field of chemistry and chemical industry.

BACKGROUND

Para-xylene (PX) is one of the basic organic raw materials in the petrochemical industry, which has a wide range of applications in chemical fiber, synthetic resins, pesticides, pharmaceuticals and polymer materials. At present, the production of para-xylene mainly uses toluene, $C_9$ aromatics and mixed xylene as raw materials, and para-xylene is obtained by disproportionation, isomerization, adsorption separation or cryogenic separation. Since the para-xylene content in the product is controlled by thermodynamics, para-xylene only accounts for ~24% of the $C_8$ mixed aromatics, and the material circulation processing amount is large during the process, and the equipment is large and the operation cost is high. In particular, the three isomers of xylene have small differences in boiling points, and it is difficult to obtain high-purity para-xylene by conventional distillation techniques, and an expensive adsorption separation process must be employed. In recent years, many patents, domestic and abroad, have disclosed a new route for the production of para-xylene. The toluene-methanol alkylation technology is a new way to produce para-xylene with high selectivity, which has been highly valued and paid great attention by the industry.

Light olefins, namely ethylene and propylene, are two basic petrochemical feedstocks that are increasingly in demand. Ethylene and propylene are mainly produced from naphtha, depending on the petroleum route. In recent years, the non-petroleum route to produce ethylene and propylene has received more and more attention, especially the process route of the methanol conversion to light olefins (MTO), which is an important way to achieve petroleum substitution strategy, reduce and alleviate our demand and dependence for petroleum.

A conventional toluene alkylation process involves mixing toluene and methanol upstream of the reactor and then feeding the mixture together into the reactor. The reactor type includes a fixed bed and a fluidized bed. In order to increase the conversion rate of toluene, the phased injection of reactants has been employed in various fixed bed and fluidized bed processes.

The competition between the MTO reaction and the alkylation reaction is a major factor affecting the conversion rate of toluene, the yield of para-xylene, and the selectivity of light olefins. The process of simultaneously realizing two reactions in the same reactor is simple, but the conversion rate of toluene is low; the process of respectively realizing two reactions in different reactors is complicated, but the conversion rate of toluene and the yield of para-xylene are higher. Therefore, the process of the alkylation of toluene and methanol to prepare para-xylene and co-produce light olefins requires a major breakthrough in the process configuration and the reactor design, thereby coordinating and optimizing the competition between the alkylation reaction and the MTO reaction, and improving the conversion rate of toluene, the yield of para-xylene and the selectivity of light olefins.

The above mentioned new routes for the preparation of para-xylene and light olefins are all acid-catalyzed reaction. Methanol-to-olefins reaction is inevitable in the process of preparing para-xylene by the alkylation of toluene and methanol based on the ZSM-5 molecular sieve catalyst. In the course of this reaction, the following reactions occur mainly:

$$C_6H_5-CH_3+CH_3OH \rightarrow C_6H_4-(CH_3)_2+H_2O \quad (1)$$

$$nCH_3OH \rightarrow (CH_2)_n+nH_2O \; n=2,3 \quad (2)$$

Methanol is both a raw material for the alkylation reaction of toluene and methanol, and a raw material for the MTO reaction, but the reaction rate of the MTO reaction is much higher than that of the alkylation reaction of toluene and methanol.

One of the characteristics of the MTO reaction is that the reaction rate is much higher than that of the alkylation reaction of toluene and methanol. Another important feature is that after the catalyst is carbonized, the conversion rate of the methanol decreases and the selectivity of the light olefins increases. Therefore, controlling the carbonation of the catalyst is an effective way to improve the selectivity of light olefins in the MTO reaction.

It can be seen from the above analysis that the technical field needs to coordinate and optimize the competition between the alkylation reaction and the MTO reaction from the two aspects of the catalyst design and the reactor design, so as to achieve synergistic effect and improve the conversion rate of toluene, the yield of para-xylene and the yield of light olefins.

SUMMARY OF THE INVENTION

According to an aspect of the present application, this is provided a fast fluidized bed reactor for preparing para-xylene and co-producing light olefins from methanol and/or dimethyl ether and toluene. The fast fluidized bed reactor resolves or improves the competition problem between an alkylation reaction and a reaction for preparing light olefins by the conversion from methanol (MTO reaction for short) during the process of producing para-xylene and co-producing light olefins from methanol and/or dimethyl ether and toluene, thus achieving a synergistic effect between the MTO reaction and the alkylation reaction. By controlling the mass transfer and reaction, the competition between the alkylation reaction and the MTO reaction is coordinated and optimized to achieve a synergistic effect, thereby improving the conversion rate of toluene, the yield of para-xylene, and the selectivity of light olefins.

As our experimental research show, when toluene and methanol are co-fed, the content of methanol in the raw material is low, the MTO reaction quickly consumes most of the methanol (alkylation reactant), inhibits the alkylation reaction of toluene and methanol, and the conversion rate of toluene is low. When the content of methanol in the raw material is excessively excessive, the difference in the diffusion speed between the methanol and toluene in the molecular sieve pores makes the adsorption amount of the toluene per unit time low, which is also unfavorable for the alkylation reaction of toluene and methanol. Therefore, optimizing the concentrations of methanol and toluene in the reaction zone is an effective way to improve the conversion rate of toluene and the yield of para-xylene.

The fast fluidized bed reactor for preparing para-xylene and co-producing light olefins from methanol and/or dimethyl ether and toluene, comprises a first reactor feed distributor and a plurality of second reactor feed distributors, the first reactor feed distributor and the plurality of second reactor feed distributors are sequentially arranged along the gas flow direction in the fast fluidized bed reactor.

Preferably, the fast fluidized bed reactor comprises a first reactor gas-solid separator and a second reactor gas-solid separator, the first reactor gas-solid separator is placed in a dilute phase zone or outside a reactor shell, and the second reactor gas-solid separator is placed in the dilute phase zone or outside the reactor shell;

the first reactor gas-solid separator is provided with a regenerated catalyst inlet, a catalyst outlet of the first reactor gas-solid separator is placed at the bottom of a reaction zone, and a gas outlet of the first reactor gas-solid separator is placed in the dilute phase zone;

an inlet of the second reactor gas-solid separator is placed in the dilute phase zone, a catalyst outlet of the second reactor gas-solid separator is placed in the reaction zone, and a gas outlet of the second reactor gas-solid separator is connected to a product gas outlet of the fast fluidized bed reactor;

the reaction zone is located at a lower part of the fast fluidized bed reactor, and the dilute phase zone is located at an upper part of the fast fluidized bed reactor.

Preferably, the first reactor gas-solid separator and the second reactor gas-solid separator are cyclone separators.

Preferably, the number of the second reactor feed distributors is in a range from 2 to 10.

Preferably, the fast fluidized bed reactor comprises a reactor heat extractor, and the reactor heat extractor is arranged inside or outside the shell of the fast fluidized bed reactor.

Further preferably, the reactor heat extractor is arranged between the plurality of reactor feed distributors.

Preferably, the fast fluidized bed reactor comprises a reactor stripper, the reactor stripper passes through the reactor shell from the outside to the inside at the bottom of the fast fluidized bed reactor and is opened in the reaction zone of the fast fluidized bed reactor, and a reactor stripping gas inlet and a spent catalyst outlet are arranged at the bottom of the reactor stripper.

Further preferably, the horizontal height of opening of the reactor stripper in the reactor shell is higher than that of the first reactor feed distributor.

In the present application, the light olefins include at least one of ethylene, propylene and butane.

In the present application, "methanol and/or dimethyl ether" means that the methanol in the feedstock may be replaced in whole or in part by dimethyl ether, including three cases: only methanol; only dimethyl ether; or both methanol and dimethyl ether.

In the present application, "methanol and/or dimethyl ether and toluene" includes three cases: methanol and toluene; dimethyl ether and toluene; or methanol, dimethyl ether and toluene.

Unless otherwise specified, the methanol in the present application may be replaced by all or part of dimethyl ether and the amount of methanol may be calculated by converting dimethyl ether into methanol having the same number of carbon atoms.

According to another aspect of the present application, there is provided a device for preparing para-xylene and co-producing light olefins from methanol and/or dimethyl ether and toluene. The device resolves or improves the competition problem between an alkylation reaction and an MTO reaction during the process of producing para-xylene and co-producing light olefins from methanol and/or dimethyl ether and toluene, thus achieving a synergistic effect between the MTO reaction and the alkylation reaction. By controlling the mass transfer and reaction, the competition between the alkylation reaction and the MTO reaction is coordinated and optimized to achieve a synergistic effect, thereby improving the conversion rate of toluene, the yield of para-xylene and the selectivity of light olefins.

The device for preparing para-xylene and co-producing light olefins from methanol and/or dimethyl ether and toluene, comprises at least one of the above-described fast fluidized bed reactors and a fluidized bed regenerator for regenerating a catalyst.

Preferably, the fluidized bed regenerator is a turbulent fluidized bed regenerator, and the fluidized bed regenerator comprises a regenerator shell, a regenerator gas-solid separator, a regenerator heat extractor and a regenerator stripper; the lower part of the fluidized bed regenerator is a regeneration zone, the upper part of the fluidized bed regenerator is a dilute phase zone of the regenerator, the regenerator feed distributor is placed at the bottom of the regeneration zone, the regenerator heat extractor is placed in the regeneration zone, and the regenerator gas-solid separator is placed in the dilute phase zone or outside the regenerator shell;

the inlet of the regenerator gas-solid separator is placed in the dilute phase zone of the regenerator, the catalyst outlet of the regenerator gas-solid separator is placed in the regeneration zone, and the regenerator stripper is opened at the bottom of the regenerator shell.

Preferably, the fluidized bed regenerator comprises a regenerator shell, a regenerator feed distributor, a regenerator gas-solid separator, a regenerator heat extractor, a flue gas outlet and a regenerator stripper;

the lower part of the fluidized bed regenerator is a regeneration zone, and the upper part of the fluidized bed regenerator is a dilute phase zone;

the regenerator feed distributor is placed at the bottom of the regeneration zone, the regenerator heat extractor is placed in the regeneration zone, the regenerator gas-solid separator is placed in the dilute phase zone or outside the regenerator shell, the inlet of the regenerator gas-solid separator is placed in the dilute phase zone, the catalyst outlet of the regenerator gas-solid separator is placed in the regeneration zone, the gas outlet of the regenerator gas-solid separator is connected to the flue gas outlet, and the regenerator stripper is opened at the bottom of the regenerator shell;

the spent catalyst outlet of the reactor stripper is connected to the inlet of an inclined spent catalyst pipe, a spent catalyst sliding valve is arranged in the inclined spent catalyst pipe, the outlet of the inclined spent catalyst pipe is connected to the inlet of a spent catalyst lift pipe, the bottom of the spent catalyst lift pipe is provided with a spent catalyst lifting gas inlet, and the outlet of the spent catalyst lift pipe is connected to the dilute phase zone of the fluidized bed regenerator;

the bottom of the regenerator stripper is provided with a regenerator stripping gas inlet, the bottom of the regenerator stripper is connected to the inlet of the inclined regenerated catalyst pipe, a regenerated catalyst sliding valve is arranged in the inclined regenerated catalyst pipe, the outlet of the inclined regenerated catalyst pipe is connected to the inlet of a regenerated catalyst lift pipe, the bottom of the regenerated catalyst lift pipe is provided with a regenerated catalyst lifting gas inlet, the outlet of the regenerated catalyst lift pipe is connected to the regenerated catalyst inlet of the first reactor gas-solid separator, and the first reactor gas-solid separator is placed in the dilute phase zone or outside the reactor shell of the fluidized bed reactor.

According to still another aspect of the present application, there is provided a method for preparing para-xylene and co-producing light olefins from methanol and/or dimethyl ether and toluene. The method resolves or improves the competition problem between an alkylation reaction and an MTO reaction during the process of producing the para-xylene and co-producing light olefins from methanol and/or dimethyl ether and toluene, thus achieving a synergistic effect between the MTO reaction and the alkylation reaction. By controlling the mass transfer and reaction, the competition between the alkylation reaction and the MTO reaction is coordinated and optimized to achieve a synergistic effect, thereby improving the conversion rate of toluene, the yield of para-xylene and the selectivity of the light olefins.

The method for preparing para-xylene and co-producing light olefins from methanol and/or dimethyl ether and toluene, at least one of the above-described fast fluidized bed reactors is used.

Preferably, a raw material A containing methanol and/or dimethyl ether and toluene is fed into the reaction zone of the fast fluidized bed reactor from the first reactor feed distributor and a raw material B containing methanol and/or dimethyl ether is respectively fed into the reaction zone of the fast fluidized bed reactor from a plurality of second reactor feed distributors to be contacted with the catalyst, to form a material stream C containing para-xylene and light olefins products and a spent catalyst.

Preferably, the material stream C is separated to obtain para-xylene, light olefins, $C_{5+}$ chain hydrocarbons, aromatic by-products and unconverted methanol, dimethyl ether and toluene;

wherein the unconverted methanol and dimethyl ether are fed to the reaction zone of the fast fluidized bed reactor from a plurality of second reactor feed distributors, the aromatic by-products and the unconverted toluene are fed into the reaction zone of the fast fluidized bed reactor from the first reactor feed distributor to be contacted with a catalyst.

Preferably, the spent catalyst is regenerated in a fluidized bed regenerator and then fed to the bottom of the reaction zone of the fast fluidized bed reactor.

Preferably, the method for preparing para-xylene and co-producing light olefins from methanol and/or dimethyl ether and toluene, comprises the steps of:

(1) feeding a material stream A containing methanol and/or dimethyl ether and toluene into the reaction zone of the fast fluidized bed reactor from a first reactor feed distributor below the fast fluidized bed reactor to be contact with the catalyst;

(2) feeding a material stream B containing methanol and/or dimethyl ether into the reaction zone of the fast fluidized bed reactor from 2 to 10 second reactor feed distributors to be in contact with the catalyst, to form a material stream C containing para-xylene and light olefins products and a spent catalyst; the 2 to 10 second reactor feed distributors are arranged in sequence above the first reactor feed distributor;

(3) separating the material stream C obtained from the step (2) to obtain a material stream C-1 containing unconverted methanol and dimethyl ether, a material stream C-2 containing aromatic by-products and unconverted toluene;

the material stream C-1 is respectively fed into the reaction zone of the fast fluidized bed reactor from the 2 to 10 second reactor feed distributors to be in contact with the catalyst; the material stream C-2 is fed into the reaction zone of the fast fluidized bed reactor from the first reactor feed distributor to be in contact with the catalyst;

the aromatic by-products comprise benzene, o-xylene, m-xylene, ethylbenzene and $C_{9+}$ aromatics;

(4) regenerating the spent catalyst obtained from the step (2) by the fluidized bed regenerator, the regenerated catalyst is gas-solid separated by the first reactor gas-solid separator, and then is fed to the bottom of the reaction zone in the fast fluidized bed reactor.

Preferably, in the mixture fed from the first reactor feed distributor into the fast fluidized bed reactor, the ratio of the molecular moles of the aromatics to the carbon moles of the methanol and/or dimethyl ether is greater than 0.5.

Further preferably, in the mixture fed from the first reactor feed distributor to the fast fluidized bed reactor, the ratio of the molecular moles of the aromatics to the carbon moles of the methanol and/or dimethyl ether is in a range from 0.5 to 5.

In the present application, the molecular mole refers to the number of moles of molecules in the substance, and the carbon mole refers to the number of moles of carbon atoms in the substance.

Preferably, the molar ratio of all oxygen-containing compounds in the mixture fed from a plurality of second reactor feed distributors into the fast fluidized bed reactor to the methanol fed from the first reactor feed distributor is greater than 1.

Further preferably, the molar ratio of all oxygen-containing compounds in the mixture fed from a plurality of second reactor feed distributors into the fast fluidized bed reactor to the methanol fed from the first reactor feed distributor is in a range from 1 to 20.

A device for regenerating a catalyst in the method for preparing para-xylene and co-producing light olefins from methanol and/or dimethyl ether and toluene use at least one of the above-described device for preparing para-xylene and co-producing light olefins from methanol and/or dimethyl ether and toluene.

Further preferably, the spent catalyst passes through the reactor stripper, the inclined spent catalyst pipe, the spent catalyst sliding valve and the spent catalyst lift pipe into the dilute phase zone of the fluidized bed regenerator;

the regeneration medium enters the regeneration zone of the fluidized bed regenerator and reacts with the spent catalyst to perform calcination to produce the flue gas containing CO and $CO_2$ and the regenerated catalyst, and the flue gas is discharged after dust removal by the regenerator gas-solid separator;

the regenerated catalyst passes through the regenerator stripper, the inclined regenerated catalyst pipe, the regenerated catalyst sliding valve and the regenerated catalyst lift pipe into the inlet of the first reactor gas-solid separator, and after the gas-solid separation, the regenerated catalyst enters the bottom of the reaction zone in the fast fluidized bed reactor;

The reactor stripping gas enters the reactor stripper via the reactor stripping gas inlet and contacts countercurrent with the spent catalyst, and then enters the fast fluidized bed reactor; the spent catalyst lifting gas enters the spent catalyst lift pipe via the spent catalyst lifting gas inlet and contacts cocurrent with the spent catalyst, and then enters the dilute phase zone of the fluidized bed regenerator;

the regenerator stripping gas enters the regenerator stripper via the regenerator stripping gas inlet and contacts countercurrent with the regenerated catalyst, and then enters the fluidized bed regenerator; the regenerated catalyst lifting gas enters the regenerated catalyst lift pipe via the regenerated catalyst lifting gas inlet and contacts concurrent with the regenerated catalyst, and then enters the inlet of the first reactor gas-solid separator, the first reactor gas-solid separator is placed in the dilute phase zone or outside the reactor shell of the fluidized bed reactor.

Preferably, the carbon content of the regenerated catalyst is less than or equal to 0.5 wt %.

Preferably, the regeneration medium is at least one of air, oxygen-poor air or water vapor; and/or, the reactor stripping gas, the regenerator stripping gas, the spent catalyst lifting gas and the regenerated catalyst lifting gas are water vapor and/or nitrogen.

Preferably, the reaction conditions in the reaction zone of the fast fluidized bed reactor are: the apparent linear velocity of gas is in a range from 1.0 m/s to 8.0 m/s, the reaction temperature is in a range from 350° C. to 600° C., the reaction pressure is in a range from 0.1 Mpa to 1.0 MPa, and the bed density is in a range from 50 kg/m$^3$ to 500 kg/m$^3$.

In the present application, in the fast fluidized bed reactor, the catalyst in a fluidized state is in the dense phase zone of the lower part and the dilute phase zone of the upper phase zone. The dense phase zone is the reaction zone of the fast fluidized bed reactor.

Preferably, the reaction conditions in the regeneration zone of the fluidized bed regenerator are: the apparent linear velocity of gas is in a range from 0.1 m/s to 2 m/s, the regeneration temperature is in a range from 500° C. to 750° C., the regeneration pressure is in a range from 0.1 MPa to 1.0 MPa, and the bed density is in a range from 200 kg/m$^3$ to 1200 kg/m$^3$.

Figure 1:
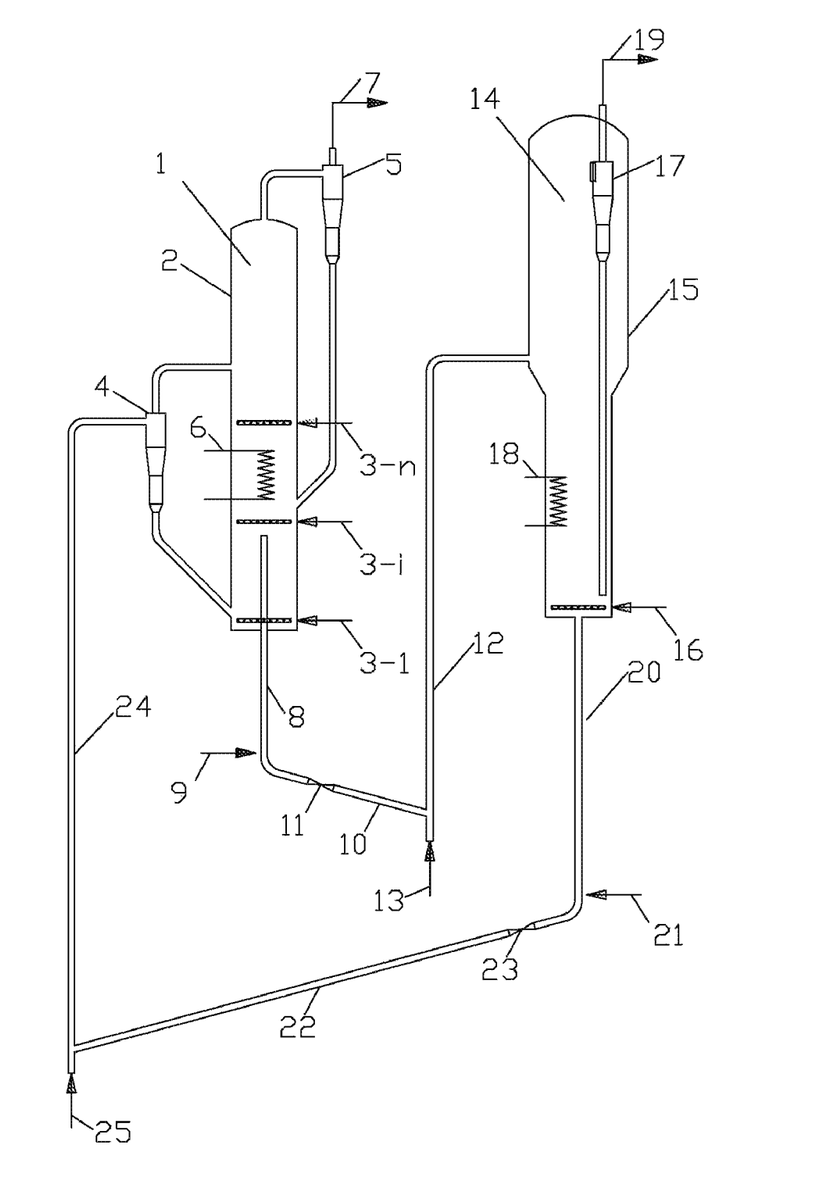
FIG. 1 is a schematic diagram of a device for producing para-xylene and co-producing light olefins from methanol and/or dimethyl ether and toluene according to an embodiment of the present application.

The present application provides a fast fluidized bed reactor for producing para-xylene and co-producing light olefins from methanol and/or dimethyl ether and toluene, the fast fluidized bed reactor comprises: a reactor shell 2, n reactor feed distributors (3-1~3-n), a reactor gas-solid separator 4, a reactor gas-solid separator 5, a reactor heat extractor 6, a product gas outlet 7 and a reactor stripper 8, wherein the lower part of the fast fluidized bed reactor 1 is a reaction zone, the upper part of the fast fluidized bed reactor 1 is a dilute phase zone, the n reactor feed distributors (3-1~3-n) are arranged from bottom to top in the reaction zone, the reactor heat extractor 6 is placed in the reaction zone or outside the reactor shell 2, the reactor gas-solid separator 4 and the reactor gas-solid separator 5 are placed in the dilute phase zone or outside the reactor shell 2, the reactor gas-solid separator 4 is provided with the regenerated catalyst inlet, the catalyst outlet of the reactor gas-solid separator 4 is located at the bottom of the reaction zone, the gas outlet of the reactor gas-solid separator 4 is located in the dilute phase zone, the inlet of the gas-solid separator 5 is located in the dilute phase zone, the catalyst outlet of the reactor gas-solid separator 5 is located in the reaction zone, the gas outlet of the reactor gas-solid separator 5 is connected to the product gas outlet 7, the reactor stripper 8 passes through the reactor shell from the outside to the inside at the bottom of the fast fluidized bed reactor and is opened in the reaction zone of the fast fluidized bed reactor 1, a reactor stripping gas inlet 9 are arranged at the bottom of the reactor stripper 8, and a spent catalyst outlet are arranged at the bottom of the reactor stripper.

In a preferred embodiment, the n reactor feed distributors (3-1~3-n) of the fast fluidized bed reactor 1 are disposed in the reaction zone from bottom to top, 3≤n≤11, and n is the total number of the reactor feed distributors.

In a preferred embodiment, the horizontal height of opening of the reactor stripper 8 in the reactor shell 2 is higher than the height of the first reactor feed distributor, so as to avoid the direct entry of fresh catalyst into the reactor stripper.

In a preferred embodiment, the reactor gas-solid separator 4 and the reactor gas-solid separator 5 are cyclone separators.

The present application further provides a device for preparing para-xylene and co-producing light olefins from methanol and/or dimethyl ether and toluene, the device comprising the fast fluidized bed reactor 1 described above and a fluidized bed regenerator 14 for regenerating a catalyst.

In a preferred embodiment, the fluidized bed regenerator 14 is a turbulent fluidized bed regenerator.

In a preferred embodiment, the fluidized bed regenerator 14 comprises a regenerator shell 15, a regenerator feed distributor 16, a regenerator gas-solid separator 17, a regenerator heat extractor 18, a flue gas outlet 19 and a regenerator stripper 20; wherein the lower part of the fluidized bed regenerator 14 is a regeneration zone, and the upper part of the fluidized bed regenerator 14 is a dilute phase zone; the regenerator feed distributor 16 is placed at the bottom of the regeneration zone, the regenerator heats extractor 18 is placed in the regeneration zone, the regenerator gas-solid separator 17 is placed in the dilute phase zone or outside the regenerator shell 15, the inlet of the regenerator gas-solid separator 17 is placed in the dilute phase zone, the catalyst outlet of the regenerator gas-solid separator 17 is placed in the regeneration zone, the gas outlet of the regenerator gas-solid separator 17 is connected to the flue gas outlet 19, the inlet of the regenerator stripper 20 is connected to the bottom of the regenerator shell 15;

the spent catalyst outlet of the reactor stripper 8 is connected to the inlet of an inclined spent catalyst pipe 10, a spent catalyst sliding valve 11 is arranged in the inclined spent catalyst pipe 10, the outlet of the inclined spent catalyst pipe 10 is connected to the inlet of a spent catalyst lift pipe 12, the bottom of the spent catalyst lift pipe 12 is provided with a spent catalyst lifting gas inlet 13, and the outlet of the spent catalyst lift pipe 12 is connected to the dilute phase zone of the fluidized bed regenerator 14; and the bottom of the regenerator stripper 20 is provided with a regenerator stripping gas inlet 21, the bottom of the regenerator stripper 20 is connected to the inlet of the inclined regenerated catalyst pipe 22, a regenerated catalyst sliding valve 23 is arranged in the inclined regenerated catalyst pipe 22, the outlet of the inclined regenerated catalyst pipe 22 is connected to the inlet of the regenerated catalyst lift pipe 24, the bottom of the regenerated catalyst lift pipe 24 is provided with a regenerated catalyst lifting gas inlet 25, the outlet of the regenerated catalyst lift pipe 24 is connected to the inlet of the reactor gas-solid separator 4.

In another aspect, the present application provides a method for preparing para-xylene and co-producing light olefins from methanol and/or dimethyl ether and toluene, comprising:

sending a raw material containing toluene and methanol from the lowermost reactor feed distributor 3-1 of the fast fluidized bed reactor 1 into the reaction zone of the fast fluidized bed reactor 1, sending methanol from the reactor feed distributors 3-2 to 3-n in the fast fluidized bed reactor 1 into the reaction zone of the fast fluidized bed reactor 1, and contacting with a catalyst, to generate a material stream containing para-xylene and light olefins product and a spent catalyst containing carbon;

sending the material stream discharged from the fast fluidized bed reactor 1 containing para-xylene and light olefins product into a product separation system, obtaining the para-xylene, ethylene, propylene, butane, $C_{5+}$ chain hydrocarbons, aromatic by-products and unconverted methanol, dimethyl ether and toluene after separation, in which aromatic by-products comprising benzene, o-xylene, m-xylene, ethylbenzene and $C_{9+}$ aromatics, sending unconverted methanol and dimethyl ether from reactor feed distributors 3-2 to 3-n into the reaction zone of the fast fluidized bed reactor 1, sending the aromatic by-products and unconverted toluene from the reactor feed distributor 3-1 into the reaction zone of the fast fluidized bed reactor 1, and contacting with a catalyst to convert to product;

regenerating the spent catalyst by a fluidized bed regenerator 14, and after being gas-solid separated by a reactor gas-solid separator 4, the regenerated catalyst is fed to the bottom of the reaction zone in the fast fluidized bed reactor 1.

In a preferred embodiment, the method described herein is carried out using the device described above for preparing para-xylene and co-producing light olefins from methanol and/or dimethyl ether and toluene.

In a preferred embodiment, the spent catalyst passes through the reactor stripper 8, the inclined spent catalyst pipe 10, the spent catalyst sliding valve 11 and the spent catalyst lift pipe 12 into the dilute phase zone of the fluidized bed regenerator 14;

a regeneration medium enters the regeneration zone of the fluidized bed regenerator 14 from the regenerator feed distributor 16 and reacts with the spent catalyst to perform calcinations to produce flue gas containing CO and $CO_2$ and the regenerated catalyst, and the flue gas is discharged after dust removal by the regenerator gas-solid separator 17;

the regenerated catalyst passes through the regenerator stripper 20, the inclined regenerated catalyst pipe 22, the regenerated catalyst sliding valve 23 and the regenerated catalyst lift pipe 24 into the inlet of the reactor gas-solid separator 4, and after gas-solid separation, the regenerated catalyst enters the bottom of the reaction zone in the fast fluidized bed reactor 1;

the reactor stripping gas enters the reactor stripper 8 via the reactor stripping gas inlet 9 and contacts countercurrent with the spent catalyst, and then enters the fast fluidized bed reactor 1; the spent catalyst lifting gas enters the spent catalyst lift pipe 12 via the spent catalyst lifting gas inlet 13 and contacts concurrent with the spent catalyst, and then enters the dilute phase zone of the fluidized bed regenerator 14;

the regenerator stripping gas enters the regenerator stripper 20 via the regenerator stripping gas inlet 21 and contacts countercurrent with the regenerated catalyst, and then enters the fluidized bed regenerator 14; the regenerated catalyst lifting gas enters the regenerated catalyst lift pipe 24 via the regenerated catalyst lifting inlet 25 and contacts concurrent with the regenerated catalyst, and then enters the inlet of the reactor gas-solid separator 4.

In the method for producing para-xylene and co-producing light olefins from methanol and/or dimethyl ether and toluene as described herein, in the mixture entering from the lowest reactor feed distributor 3-1 of the fast fluidized bed reactor, the amount of substance ratio of the aromatics to the methanol is greater than 0.5, further preferably, greater than 1.

In the method for producing para-xylene and co-producing of light olefins from methanol and/or dimethyl ether and toluene as described herein, the amount of substance ratio of the oxygen-containing compounds entering from the reactor feed distributors 3-2 to 3-n and the methanol entering from the reactor feed distributor 3-1 is greater than 1, more preferably greater than 5.

In a preferred embodiment, the catalyst comprises a HZSM-5 molecular sieve having both the functions of the alkylation of methanol and/or dimethyl ether with toluene, and the aromatization of preparing olefins from methanol and methanol.

In a preferred embodiment, the catalyst comprises a HZSM-11 molecular sieve having both the functions of the alkylation of methanol and/or dimethyl ether with toluene, and the aromatization of preparing olefins from methanol and methanol.

In a preferred embodiment, the carbon content of the regenerated catalyst is less than 0.5 wt. %, and further preferably, the carbon content of the regenerated catalyst is less than 0.1 wt. %.

In a preferred embodiment, the reaction conditions of the reaction zone of the fast fluidized bed reactor are: the apparent linear velocity of gas is in a range from 1.0 m/s to 8.0 m/s, the reaction temperature is in a range from 350° C. to 600° C., the reaction pressure is in a range from 0.1 MPa to 1.0 MPa, and the bed density is in a range from 50 kg/m³ to 500 kg/m³.

In a preferred embodiment, the reaction conditions in the regeneration zone of the fluidized bed regenerator are: the apparent linear velocity of gas is in a range from 0.1 m/s to 2 m/s, the regeneration temperature is in a range from 500° C. to 750° C., the regeneration pressure is in a range from 0.1 MPa to 1.0 MPa, and the bed density is in a range from 200 kg/m³ to 1200 kg/m³.

In a preferred embodiment, the regeneration medium is any one of air, oxygen-poor air or water vapor or a mixture thereof; the reactor stripping gas, the regenerator stripping gas, the spent catalyst lifting gas and the regenerated catalyst lifting gas are water vapor or nitrogen.

In the method for producing para-xylene and co-producing light olefins from methanol and/or dimethyl ether and toluene as described in the present application, the conversion rate of toluene is greater than 50%, the conversion rate of methanol is greater than 70%, the selectivity of para-xylene is greater than 90%, the single-pass yield of para-xylene based on aromatics is greater than 48%, and the selectivity of light olefins (ethylene+propylene+butane) in chain hydrocarbons is greater than 70%, and good technical results have been achieved.

The main characteristics of the fast fluidized bed reactor in the present application are that the aromatic feedstock enter from the lowermost reactor feed distributor, the oxygen-containing compound enters from n reactor feed distributors respectively, and the highly active regenerated catalyst directly enters the bottom of the reaction zone. The aromatic feedstock comprises fresh toluene, unconverted toluene and aromatic by-products, and the oxygen-containing compound comprises fresh methanol, unconverted methanol and dimethyl ether. First, in the lower part of the reaction zone, the catalyst activity has a high activity, which is advantageous to the alkylation reaction of toluene, the isomerization reaction of aromatic hydrocarbon by-products and methyl transfer reaction, etc.; second, using the method of multi-stage feeding of oxygen-containing compound, only a small portion of the oxygen-containing compound is fed from the bottom of the reactor, the low concentration of oxygen-containing compound in the bottom region and the high concentrations of aromatics weaken the adsorption competition of oxygen-containing compound with fast diffusion rate in the molecular sieve pores to the aromatic hydrocarbons with slow diffusion rate, so as to ensure that most of the aromatics are adsorbed in the catalyst in the bottom region; third, most of the oxygen-containing compounds are fed from the middle part and the upper part, and the conversion reaction of the oxygen-containing compound mainly occurs in the middle part and the upper part of the reaction zone, so as to avoid rapidly decreased activity of the high activity of the regenerated catalyst in the bottom zone due to carbon formation during the MTO reaction; fourth, the amount of carbon in the catalyst is higher in the middle part and the upper part of the reaction zone, which is advantageous to improve the selectivity of light olefins in the MTO reaction; fifth, using the method of multi-stage feeding of the oxygen-containing compound, the concentration distribution of the oxygen-containing compound in the reaction zone is relatively uniform, providing sufficient alkylation reactants. After the aromatic hydrocarbons adsorbed in the catalyst are contacted with the alkylation reactants, the alkylation reaction rapidly occurs to improve the conversion rate of toluene and the yield of para-xylene.

In summary, the fast fluidized bed reactor in the present application can coordinate and optimize the competition between the alkylation reaction of toluene and methanol and the MTO reaction to achieve a synergistic effect, thereby improving the conversion rate of toluene, the yield of para-xylene and the yield of light olefins.

From the viewpoint of reactor design and process configuration, the present application coordinates and optimizes the competition between the alkylation reaction and the MTO reaction by controlling the concentrations of methanol and/or dimethyl ether relative to toluene, and improves the yield of para-xylene and the selectivity of light olefins to ensure that neither the situation of the inhibition of the alkylation reaction occurs due to the rapid consumption of most methanol and/or dimethyl ether by the MTO reaction, nor the situation against the alkylation reaction occurs due to far excess content of methanol and/or dimethyl, a large number of the MTO reaction occur, and lower adsorption amount of toluene in the catalyst per unit time.

The benefits that brought out by the present application include:

(1) this is provided a fluidized bed reactor and device to achieve mass transfer and reaction control by distributing different raw material stream in different regions in a co-feed system with a large difference in raw material reaction rates, so as to coordinate and optimize a co-feed system, coordinate and optimize the competition between the alkylation reaction and the MTO reaction to achieve a synergistic effect, thereby improving the conversion rate of toluene, the yield of para-xylene and the selectivity of light olefins.

(2) The method for producing para-xylene and co-producing light olefins from methanol and toluene, provided by the present application, has higher conversion rate of toluene and the selectivity of para-xylene, the conversion rate of toluene is greater than 50%, the selectivity of para-xylene in the xylene isomer in the product is greater than 90%, the mass single-pass yield of para-xylene based on aromatics is greater than 48%, and good technical effect have been achieved.

The reference numerals in the drawings are as follows:
1—fast fluidized bed reactor; 2—reactor shell; 3—reactor feed distributors (3-1~3-n); 4—reactor gas-solid separator; 5—reactor gas-solid separator; 6—reactor heat extractor; 7—product gas outlet; 8—reactor stripper; 9—reactor stripping gas inlet; 10—inclined spent catalyst pipe; 11—spent catalyst sliding valve; 12—spent catalyst lift pipe; 13—spent catalyst lifting gas inlet; 14—fluidized bed regenerator; 15—regenerator shell; 16—regenerator feed distributor; 17—regenerator gas-solid separator; 18—regenerator heat extractor; 19—flue gas outlet; 20—regenerator stripper; 21—regenerator stripping gas inlet; 22—inclined regenerated catalyst pipe; 23—regenerated catalyst sliding valve; 24—regenerated catalyst lift pipe; 25—regenerated catalyst lifting gas inlet.

DETAILED DESCRIPTION

The present application will be described in detail below with reference to the embodiments, but the application is not limited to the embodiments.

Unless otherwise specified, the raw materials and catalysts in the embodiments of the present application are commercially available.

As an embodiment of the present application, a schematic diagram of a device for producing para-xylene and co-producing light olefins from methanol and/or dimethyl ether and toluene is shown in FIG. 1. The device comprises: the fast fluidized bed reactor 1, which comprises a reactor shell 2, n reactor feed distributors 3-1 to 3-n (the distributors between 3-1 and 3-n in FIG. 1 takes 3-i as an example), a reactor gas-solid separator 4, a reactor gas-solid separator 5, a reactor heat extractor 6, a product gas outlet 7 and a reactor stripper 8, wherein the lower part of the fast fluidized bed reactor 1 is a reaction zone, the upper part of the fast fluidized bed reactor 1 is a dilute phase zone, the n reactor feed distributors 3-1 to 3-n are arranged from bottom to top in the reaction zone, $3 \leq n \leq 11$, the reactor heat extractor 6 is placed in the reaction zone or outside the reactor shell 2, the reactor gas-solid separator 4 and the reactor gas-solid separator 5 are placed in the dilute phase zone or outside the reactor shell 2, the inlet of the reactor gas-solid separator 4 is connected to the regenerated catalyst lift pipe 24, the catalyst outlet of the reactor gas-solid separator 4 is located at the bottom of the reaction zone, the gas outlet of the reactor gas-solid separator 4 is located in the dilute phase zone, the inlet of the reactor gas-solid separator 5 is located in the dilute phase zone, the catalyst outlet of the reactor gas-solid separator 5 is located in the reaction zone, the gas outlet of the reactor gas-solid separator 5 is connected to the product gas outlet 7, the inlet of the reactor stripper 8 is in the reaction zone of the fast fluidized bed reactor 1, with the horizontal height than that of the first reactor feed distributor.

As shown in FIG. 1, the device comprises: a fluidized bed regenerator 14 comprising a regenerator shell 15, a regenerator feed distributor 16, a regenerator gas-solid separator 17, a regenerator heat extractor 18, a flue gas outlet 19 and a regenerator stripper 20, wherein the lower part of the fluidized bed regenerator 14 is a regeneration zone, the upper part of the fluidized bed regenerator 14 is a dilute phase zone, the regenerator feed distributor 16 is placed at the bottom of the regeneration zone, the regenerator heat extractor 18 is placed in the regeneration zone, the regenerator gas-solid separator 17 is placed in the dilute phase zone or outside the regenerator shell 15, the inlet of the regenerator gas-solid separator 17 is placed in the dilute phase zone, the catalyst outlet of the regenerator gas-solid separator 17 is placed in the regeneration zone, the gas outlet of the regenerator gas-solid separator 17 is connected to the flue gas outlet 19, and the inlet of the regenerator stripper 20 is connected to the bottom of the regenerator shell 15.

As shown in FIG. 1, the bottom of the reactor stripper 8 is provided with a reactor stripping gas inlet 9, the bottom of the reactor stripper 8 is connected to the inlet of the inclined spent catalyst pipe 10, a spent catalyst sliding valve 11 is arranged in the inclined spent catalyst pipe 10, the outlet of the inclined spent catalyst pipe 10 is connected to the inlet of a spent catalyst lift pipe 12, the bottom of the spent catalyst lift pipe 12 is provided with a spent catalyst lifting gas inlet 13, and the outlet of the spent catalyst lift pipe 12 is connected to the dilute phase zone of the fluidized bed regenerator 14;

As shown in FIG. 1, the bottom of the regenerator stripper 20 is provided with a regenerator stripping gas inlet 21, the bottom of the regenerator stripper 20 is connected to the inlet of the inclined regenerated catalyst pipe 22, a regenerated catalyst sliding valve 23 is arranged in the inclined regenerated catalyst pipe 22, the outlet of the inclined regenerated catalyst pipe 22 is connected to the inlet of the regenerated catalyst lift pipe 24, the bottom of the regenerated catalyst lift pipe 24 is provided with a regenerated catalyst lifting gas inlet 25, and the outlet of the regenerated catalyst lift pipe 24 is connected to the inlet of the reactor gas-solid separator 4.

In the above embodiment of the present application, the fluidized bed regenerator 14 may be a turbulent fluidized bed regenerator; the reactor gas-solid separator 4, the reactor gas-solid separator 5 and the regenerator gas-solid separator 17 may be cyclone separators.

As a specific embodiment of the present application, the method according to the present application for producing para-xylene and co-producing light olefins from methanol and/or dimethyl and toluene comprises:

a) sending a raw material containing toluene and methanol from the lowermost reactor feed distributor 3-1 of the fast fluidized bed reactor 1 into the reaction zone of the fast fluidized bed reactor 1, sending methanol from the reactor feed distributors 3-2 to 3-*n* in the fast fluidized bed reactor 1 into the reaction zone of the fast fluidized bed reactor 1, and contacting with a catalyst, to generate a material stream containing para-xylene and light olefins products and a spent catalyst containing carbon;

b) sending the material stream discharged from the fast fluidized bed reactor 1 containing para-xylene and light olefins product into a product separation system, obtaining para-xylene, ethylene, propylene, butane, $C_{5+}$ chain hydrocarbons, aromatic hydrocarbon by-products and unconverted methanol, dimethyl ether and toluene after separation, in which aromatic by-products comprising benzene, o-xylene, m-xylene, ethylbenzene and $C_{9+}$ aromatics, sending unconverted methanol and dimethyl ether from the reactor feed distributor 3-2 to 3-*n* into the reaction zone of the fast fluidized bed reactor 1, sending the aromatic by-products and unconverted toluene from the reactor feed distributor 3-1 into the reaction zone of the fast fluidized bed reactor 1, and contacting with a catalyst to convert to product;

c) the spent catalyst passes through the reactor stripper 8, the inclined spent catalyst pipe 10, the spent catalyst sliding valve 11 and the spent catalyst lift pipe 12 into the dilute phase zone of the fluidized bed regenerator 14;

d) the regeneration medium enters the regeneration zone of the fluidized bed regenerator 14 from the regenerator feed distributor 16, the regeneration medium reacts with the spent catalyst to perform calcination to produce a flue gas containing CO and $CO_2$ and a regenerated catalyst, and the flue gas is discharged after dust removal by the regenerator gas-solid separator 17;

e) the regenerated catalyst passes through the regenerator stripper 20, the inclined regenerated catalyst pipe 22, the regenerated catalyst sliding valve 23 and the regenerated catalyst lift pipe 24 into the inlet of the reactor gas-solid separator 4, and after gas-solid separation, the regenerated catalyst enters the bottom of the reaction zone of the fast fluidized bed reactor 1;

f) the reactor stripping gas enters the reactor stripper 8 via the reactor stripping gas inlet 9 and contacts countercurrent with the spent catalyst, and then enters the fast fluidized bed reactor 1; the spent catalyst lifting gas enters the spent catalyst lift pipe 12 via the spent catalyst lifting gas inlets 13 and contacts concurrent with the spent catalyst, and then enters the dilute phase zone of the fluidized bed regenerator 14;

g) the regenerator stripping gas enters the regenerator stripper 20 via the regenerator stripping gas inlet 21 and contacts countercurrent with the regenerated catalyst, and then enters the fluidized bed regenerator 14; the regenerated catalyst lifting gas enters the regenerated catalyst lift pipe 24 via the regenerated catalyst lifting gas inlet 25 and contacts cocurrent with the regenerated catalyst, and then enters the inlet of the reactor gas-solid separator 4.

In order to better illustrate the present application and facilitate the understanding of the technical scheme of the present application, representative but non-restrictive examples of the present application are listed as follows.

Example 1

The device shown in FIG. 1 is employed, but the reactor gas-solid separator 4 is not included in the fast fluidized bed reactor 1, and the regenerated catalyst lift pipe 24 is directly connected to the dilute phase zone of the fast fluidized bed reactor 1. The fast fluidized bed reactor 1 contains one reactor feed distributor 3-1.

The reaction conditions in the reaction zone of the fast fluidized bed reactor 1 are as follows: the apparent linear velocity of gas is about 1.0 m/s, the reaction temperature is about 500° C., the reaction pressure is about 0.15 MPa, and the bed density is about 350 kg/m³.

The reaction conditions of the regeneration zone of the fluidized bed regenerator 14 are as follows: the apparent linear velocity of gas is about 1.0 m/s, the regeneration temperature is about 650° C., the regeneration pressure is about 0.15 MPa, and the bed density is about 350 kg/m³.

The catalyst contains a HZSM-5 molecular sieve. The carbon content of the regenerated catalyst is a about 0.2 wt. %.

The regeneration medium is air; the reactor stripping gas, the regenerator stripping gas, the spent catalyst lifting gas and the regenerated catalyst lifting gas are water vapor.

In the mixture entering from the lowest reactor feed distributor 3-1 of the fast fluidized bed reactor, the mass ratio of aromatics to methanol is 0.5.

The results show that the conversion rate of toluene is 22%, the conversion rate of methanol is 95%, the selectivity of para-xylene is 99%, the single-pass yield of para-xylene based on aromatics is 21%, and the selectivity of light olefins (ethylene+propylene+butane) in chain hydrocarbons is 64%.

Example 2

The device shown in FIG. 1 is employed, the fast fluidized bed reactor 1 contains three reactor feed distributors 3-1 to 3-3, and the reactor gas-solid separator 4 is placed outside the reactor shell 2.

The reaction conditions of the reaction zone of the fast fluidized bed reactor 1 are as follows: the apparent linear velocity of gas is about 1.0 m/s, the reaction temperature is about 500° C., the reaction pressure is about 0.15 MPa, and the bed density is about 350 kg/m$^3$.

The reaction conditions in the regeneration zone of the fluidized bed regenerator 14 are as follows: the apparent linear velocity of gas is about 1.0 m/s, the regeneration temperature is about 650° C., the regeneration pressure is about 0.15 MPa, and the bed density is about 350 kg/m$^3$.

The catalyst contains a HZSM-5 molecular sieve. The carbon content of the regenerated catalyst is about 0.2 wt. %.

The regeneration medium is air; the reactor stripping gas, the regenerator stripping gas, the spent catalyst lifting gas, and the regenerated catalyst lifting gas are water vapor.

In the mixture entering from the lowest reactor feed distributor 3-1 of the fast fluidized bed reactor, the mass ratio of aromatics to methanol is 2.

The mass ratio of the oxygen-containing compounds entering from the reactor feed distributors 3-2 to 3-3 and the methanol entering from the reactor feed distributor 3-1 is 3.

The results show that the conversion rate of toluene is 50%, the conversion rate of methanol is 93%, the selectivity of para-xylene is 96%, and the single-pass yield of para-xylene based on aromatics is 48%, and the selectivity of light olefins (ethylene+propylene+butane) in chain hydrocarbons is 72%.

The present example is different from Example 1 in that
1. the regenerated catalyst enters the bottom of the fast fluidized bed reactor, while the regenerated catalyst of Example 1 enters the dilute phase zone of the fast fluidized bed reactor;
2. methanol is separately fed from three reactor feed distributors (3-1 to 3-3), while the methanol in Example 1 is fed from one reactor feed distributor 3-1.

Comparing the present example with Example 1, it can be seen that the catalyst is first exposed to a high concentration of aromatic raw material, and the conversion rate of toluene, the yield of para-xylene and the selectivity of light olefins are greatly improved.

Example 3

The device shown in FIG. 1 is employed, the fast fluidized bed reactor 1 contains six reactor feed distributors 3-1 to 3-6, and the reactor gas-solid separator 4 is placed inside the reactor shell 2.

The reaction conditions in the reaction zone of the fast fluidized bed reactor 1 are as follows: the apparent linear velocity of gas is about 6.0 m/s, the reaction temperature is about 570° C., the reaction pressure is about 0.7 MPa, and the bed density is about 60 kg/m$^3$.

The reaction conditions in the regeneration zone of the fluidized bed regenerator 14 are as follows: the apparent linear velocity of gas is about 1.7 m/s, the regeneration temperature is about 600° C., the regeneration pressure is about 0.7 MPa, and the bed density is about 220 kg/m$^3$.

The catalyst contains a HZSM-11 molecular sieve. The carbon content of the regenerated catalyst is about 0.1 wt. %.

The regeneration medium is air; the reactor stripping gas, the regenerator stripping gas, the spent catalyst lifting gas and the regenerated catalyst lifting gas are water vapor.

In the mixture entering from the lowest reactor feed distributor 3-1 of the fast fluidized bed reactor, the mass ratio of aromatics to methanol is 4.

The mass ratio of the oxygen-containing compounds entering from the reactor feed distributors 3-2 to 3-6 and methanol entering from the reactor feed distributor 3-1 is 20.

The results show that the conversion of toluene is 55%, the conversion rate of methanol is 74%, the selectivity of para-xylene is 90%, the single-pass yield of para-xylene based on aromatics is 58%, and the selectivity of light olefins (ethylene+propylene+butane) in chain hydrocarbons is 73%.

Example 4

The device shown in FIG. 1 is employed, the fast fluidized bed reactor 1 contains four reactor feed distributors 3-1 to 3-4, and the reactor gas-solid separator 4 is placed outside the reactor shell 2.

The reaction conditions in the reaction zone of the fast fluidized bed reactor 1 are as follows: the apparent linear velocity of gas is about 3.0 m/s, the reaction temperature is about 420° C., the reaction pressure is about 0.3 MPa, and the bed density is about 180 kg/m$^3$.

The reaction conditions in the regeneration zone of the fluidized bed regenerator 14 are as follows: the apparent linear velocity of gas is about 1.2 m/s, the regeneration temperature is about 700° C., the regeneration pressure is about 0.3 MPa, and the bed density is about 330 kg/m$^3$.

The catalyst contains a HZSM-5 molecular sieve. The carbon content of the regenerated catalyst is about 0.1 wt. %.

The regeneration medium is water vapor; the reactor stripping gas, the regenerator stripping gas, the spent catalyst lifting gas and the regenerated catalyst lifting gas are nitrogen.

In the mixture entering from the lowest reactor feed distributor 3-1 of the fast fluidized bed reactor, the mass ratio of aromatics to methanol is 3.

The mass ratio of the oxygen-containing compounds entering from the reactor feed distributors 3-1 to 3-4 and methanol entering from the reactor feed distributor 3-1 is 10.

The results show that the conversion rate of toluene is 52%, the conversion rate of methanol is 83%, the selectivity of para-xylene is 91%, the single-pass yield of para-xylene based on aromatics is 53%, and the selectivity of light olefins (ethylene+propylene+butane) in chain hydrocarbons is 71%.

While the present application has been described above with reference to preferred embodiments, but these embodiments are not intended to limit the claims. Without departing from the spirit of the present application, people skilled in the art will be able to make several possible variations and modifications and thus the protection scope shall be determined by the scope as defined in the claims.

The invention claimed is:
1. A fluidized bed reactor for preparing para-xylene and co-producing light olefins from methanol and/or dimethyl ether and toluene, wherein, a lower part of the fluidized bed reactor is a reaction zone, and an upper part of the fluidized bed reactor is a dilute phase zone, the fluidized bed reactor comprises a reactor shell, a first reactor feed distributor and a plurality of second reactor feed distributors, the first reactor feed distributor and the plurality of second reactor feed distributors are sequentially arranged from bottom to top in the reaction zone; and wherein, the fluidized bed reactor comprises a first reactor gas-solid separator, the first reactor gas-solid separator is placed in the dilute phase zone or outside the reactor shell, the first reactor gas-solid separator is provided with a regenerated catalyst inlet, a catalyst outlet of the first reactor gas-solid separator is placed at the bottom of a reaction zone, and a gas outlet of the first reactor gas-solid separator is placed in the dilute phase zone.

2. The fluidized bed reactor of claim 1, wherein the fluidized bed reactor comprises a first reactor gas-solid separator and a second reactor gas-solid separator, the first reactor gas-solid separator is placed in a dilute phase zone or outside the reactor shell, and the second reactor gas-solid separator is placed in the dilute phase zone or outside the reactor shell;

an inlet of the second reactor gas-solid separator is placed in the dilute phase zone, a catalyst outlet of the second reactor gas-solid separator is placed in the reaction zone, and a gas outlet of the second reactor gas-solid separator is connected to a product gas outlet of the fluidized bed reactor;

wherein the first reactor gas-solid separator and the second reactor gas-solid separator are cyclone separators.

3. The fluidized bed reactor of claim 1, wherein the number of the second reactor feed distributors is in a range from 2 to 10.

4. The fluidized bed reactor of claim 1, wherein the fluidized bed reactor comprises a reactor heat extractor, and the reactor heat extractor is arranged inside or outside the shell of the fluidized bed reactor.

5. The fluidized bed reactor of claim 1, wherein the fluidized bed reactor comprises a reactor stripper, the reactor stripper passes through the reactor shell from the outside to the inside at the bottom of the fluidized bed reactor and is opened in the reaction zone of the fluidized bed reactor, and a reactor stripping gas inlet and a spent catalyst outlet are arranged at the bottom of the reactor stripper;

wherein the horizontal height of opening of the reactor stripper in the reactor shell is higher than that of the first reactor feed distributor.

6. A device for preparing para-xylene and co-producing light olefins from methanol and/or dimethyl ether and toluene, wherein the device comprises the fluidized bed reactor according to claim 1 and a fluidized bed regenerator for regenerating a catalyst.

7. The device of claim 6, wherein the fluidized bed regenerator is a turbulent fluidized bed regenerator, and the fluidized bed regenerator comprises a regenerator shell, a regenerator gas-solid separator, a regenerator heat extractor and a regenerator stripper; a lower part of the fluidized bed regenerator is a regeneration zone, an upper part of the fluidized bed regenerator is a dilute phase zone of the regenerator, a regenerator feed distributor is placed at the bottom of the regeneration zone, the regenerator heat extractor is placed in the regeneration zone, and the regenerator gas-solid separator is placed in the dilute phase zone or outside the regenerator shell; and an inlet of the regenerator gas-solid separator is placed in the dilute phase zone of the regenerator, a catalyst outlet of the regenerator gas-solid separator is placed in the regeneration zone, and the regenerator stripper is opened at the bottom of the regenerator shell.

8. The device of claim 6, wherein the fluidized bed regenerator comprises a regenerator shell, a regenerator feed distributor, a regenerator gas-solid separator, a regenerator heat extractor, a flue gas outlet and a regenerator stripper;

a lower part of the fluidized bed regenerator is a regeneration zone, and an upper part of the fluidized bed regenerator is a dilute phase zone;

a regenerator feed distributor is placed at the bottom of the regeneration zone, a regenerator heat extractor is placed in the regeneration zone, the regenerator gas-solid separator is placed in the dilute phase zone or outside the regenerator shell, an inlet of the regenerator gas-solid separator is placed in the dilute phase zone, a catalyst outlet of the regenerator gas-solid separator is placed in the regeneration zone, a gas outlet of the regenerator gas-solid separator is connected to the flue gas outlet, and the regenerator stripper is opened at the bottom of the regenerator shell;

a spent catalyst outlet of the reactor stripper is connected to an inlet of an inclined spent catalyst pipe, a spent catalyst sliding valve is arranged in the inclined spent catalyst pipe, an outlet of the inclined spent catalyst pipe is connected to an inlet of a spent catalyst lift pipe, a bottom of the spent catalyst lift pipe is provided with a spent catalyst lifting gas inlet, and an outlet of the spent catalyst lift pipe is connected to the dilute phase zone of the fluidized bed regenerator; and a bottom of the regenerator stripper is provided with a regenerator stripping gas inlet, the bottom of the regenerator stripper is connected to an inlet of an inclined regenerated catalyst pipe, a regenerated catalyst sliding valve is arranged in the inclined regenerated catalyst pipe, an outlet of the inclined regenerated catalyst pipe is connected to the inlet of a regenerated catalyst lift pipe, a bottom of the regenerated catalyst lift pipe is provided with a regenerated catalyst lifting gas pipe, an outlet of the regenerated catalyst lift pipe is connected to the regenerated catalyst inlet of the first reactor gas-solid separator.

9. A method for preparing para-xylene and co-producing light olefins from methanol and/or dimethyl ether and toluene, wherein the fluidized bed reactors according to claim 1 is used.

10. The method of claim 9, wherein a raw material A containing methanol and/or dimethyl ether and toluene is fed into the reaction zone of the fluidized bed reactor from the first reactor feed distributor and a raw material B containing methanol and/or dimethyl ether is fed into the reaction zone of the fluidized bed reactor from a plurality of second reactor feed distributors respectively to be in contact with a catalyst, to form a material stream C containing para-xylene, light olefins products and a spent catalyst.

11. The method of claim 10, wherein the material stream C is separated to obtain para-xylene, light olefins, $C_{5+}$ chain hydrocarbons, aromatic by-products, unconverted methanol, dimethyl ether and toluene;

wherein the unconverted methanol and dimethyl ether are fed into the reaction zone of the fluidized bed reactor from a plurality of second reactor feed distributors, the aromatic by-products and the unconverted toluene are fed into the reaction zone of the fluidized bed reactor from the first reactor feed distributor to be in contact with a catalyst.

12. The method of claim 10, wherein the spent catalyst is regenerated in a fluidized bed regenerator and fed to the bottom of the reaction zone of the fluidized bed reactor.

13. The method of claim 9, wherein the method comprises the steps of:

(1) feeding a material stream A containing methanol and/or dimethyl ether and toluene into the reaction zone of the fluidized bed reactor from a first reactor feed distributor below the fluidized bed reactor to be in contact with a catalyst;

(2) feeding a material stream B containing methanol and/or dimethyl into the reaction zone of the fluidized bed reactor from 2 to 10 second reactor feed distributors to be in contact with the catalyst, to form a material stream C containing para-xylene, light olefins products and a spent catalyst; the 2 to 10 second reactor feed distributors are arranged in sequence above the first reactor feed distributor;

(3) separating the material stream C obtained from the step (2) to obtain a material stream C-1 containing unconverted methanol and dimethyl ether, a material stream C-2 containing aromatic by-products and unconverted toluene; the material stream C-1 is respectively fed into the reaction zone of the fluidized bed reactor from the 2 to 10 second reactor feed distributors to be in contact with the catalyst; the material stream C-2 is fed into the reaction zone of the fluidized bed reactor from the first reactor feed distributor to be in contact with the catalyst;

the aromatic by-products comprise benzene, o-xylene, m-xylene, ethylbenzene and $C_{9+}$ aromatics;

(4) regenerating the spent catalyst obtained from the step (2) by a fluidized bed regenerator, a regenerated catalyst is gas-solid separated by the first reactor gas-solid separator, and then is fed to the bottom of the reaction zone in the fluidized bed reactor.

14. The method of claim 10, wherein in the mixture fed from the first reactor feed distributor into the fluidized bed reactor, the ratio of the molecular moles of aromatics to the carbon moles of methanol and/or dimethyl ether is greater than 0.5;

wherein the molar ratio of all oxygen-containing compounds in the raw material B fed from a plurality of second reactor feed distributors into the fluidized bed reactor to the methanol fed from the first reactor feed distributor is greater than 1.

15. The method of claim 9, wherein a catalyst regeneration employs at least one device for preparing para-xylene and co-producing light olefins from methanol and/or dimethyl ether and toluene, wherein the device comprises at least one fluidized bed reactor for preparing para-xylene and co-producing light olefins from methanol and/or dimethyl ether and toluene, and a fluidized bed regenerator for regenerating a catalyst.

16. The method of claim 15, wherein the spent catalyst passes through a reactor stripper, an inclined spent catalyst pipe, a spent catalyst sliding valve and a spent catalyst lift pipe into a dilute phase zone of the fluidized bed regenerator;

a regeneration medium enters the regeneration zone of the fluidized bed regenerator and reacts with the spent catalyst to perform calcination to produce a flue gas containing CO and $CO_2$ and a regenerated catalyst, and the flue gas is discharged after dust removal by a regenerator gas-solid separator;

a regenerated catalyst passes through a regenerator stripper, an inclined regenerated catalyst pipe, a regenerated catalyst sliding valve and a regenerated catalyst lift pipe into the inlet of the first reactor gas-solid separator, and after the gas-solid separation, the regenerated catalyst enters the bottom of the reaction zone in the fluidized bed reactor;

a reactor stripping gas enters a reactor stripper via a reactor stripping gas inlet and contacts countercurrent with the spent catalyst, and then enters the fluidized bed reactor; a spent catalyst lifting gas enters the spent catalyst lift pipe via a spent catalyst lifting gas inlet and contacts cocurrent with the spent catalyst, and then enters the dilute phase zone of the fluidized bed regenerator;

a regenerator stripping gas enters the regenerator stripper via a regenerator stripping gas inlet and contacts countercurrent with the regenerated catalyst, and then enters the fluidized bed regenerator; a regenerated catalyst lifting gas enters the regenerated catalyst lift pipe via a regenerated catalyst lifting gas inlet and contacts concurrent with the regenerated catalyst, and then enters an inlet of the first reactor gas-solid separator.

17. The method of claim 16, wherein the carbon content of the regenerated catalyst is less than or equal to 0.5 wt %.

18. The method of claim 16, wherein the regeneration medium is at least one of air, oxygen-poor air or water vapor; and/or the reactor stripping gas, the regenerator stripping gas, the spent catalyst lifting gas and the regenerated catalyst lifting gas are water vapor and/or nitrogen.

19. The method of claim 9, wherein the reaction conditions in the reaction zone of the fluidized bed reactor are: the apparent linear velocity of gas is in a range from 1.0 m/s to 8.0 m/s, the reaction temperature is in a range from 350° C. to 600° C., the reaction pressure is in a range from 0.1 MPa to 1.0 MPa, and the bed density is in a range from 50 kg/m³ to 500 kg/m³.

20. The method of claim 12, wherein the reaction conditions in a regeneration zone of the fluidized bed regenerator are: the apparent linear velocity of gas is in a range from 0.1 m/s to 2 m/s, the regeneration temperature is in a range from 500° C. to 750° C., the regeneration pressure is in a range from 0.1 MPa to 1.0 MPa, and the bed density is in a range from 200 kg/m³ to 1200 kg/m³.

* * * * *